(12) United States Patent
Francis

(10) Patent No.: US 6,821,185 B1
(45) Date of Patent: Nov. 23, 2004

(54) MATERNITY BRA

(76) Inventor: Euta D. Francis, 5802 Snyder Ave., Brooklyn, NY (US) 11203

( * ) Notice: Subject to any disclaimer, the term of this patent is extended or adjusted under 35 U.S.C. 154(b) by 0 days.

(21) Appl. No.: 10/445,440

(22) Filed: May 28, 2003

(51) Int. Cl.[7] .................................................. A41C 3/00
(52) U.S. Cl. .......................................... 450/36; 450/37
(58) Field of Search .............................. 450/36–38, 56, 450/57, 58, 54; 2/104, 106, 109, 267; 604/74.75, 73, 315, 346; 128/898; 54/20, 58, 59

(56) References Cited

U.S. PATENT DOCUMENTS

| | | | | |
|---|---|---|---|---|
| 2,452,345 A | * | 10/1948 | Anselmo | 450/57 |
| 6,004,186 A | * | 12/1999 | Penny | 450/36 |
| 6,027,396 A | * | 2/2000 | Yonchar | 450/36 |
| 6,213,840 B1 | * | 4/2001 | Han | 450/36 |
| 6,227,936 B1 | * | 5/2001 | Mendoza | 450/36 |

* cited by examiner

*Primary Examiner*—Gloria M. Hale

(57) ABSTRACT

A bra for use while pumping breast milk including a slot in the breast section of the bra for use with a breast pump funnel and a padded area surrounding each slot to support the funnel. Optionally, the bra may be provided as part of a kit for pumping breast milk that includes a pump funnel adapted for use in pumping breast milk and a bra. The bra has a slot in the approximate center of each breast section and a padded area surrounding each slot. Each slot is adapted to provide access for the breast pump funnel, and each padded area is adapted to provide extra support for the pump funnel while engaged. A method of pumping breast milk includes the steps of wearing the bra having slots and padded breast pump funnel supports; inserting a pump funnel through one slot; and pumping breast milk through the funnel.

9 Claims, 2 Drawing Sheets

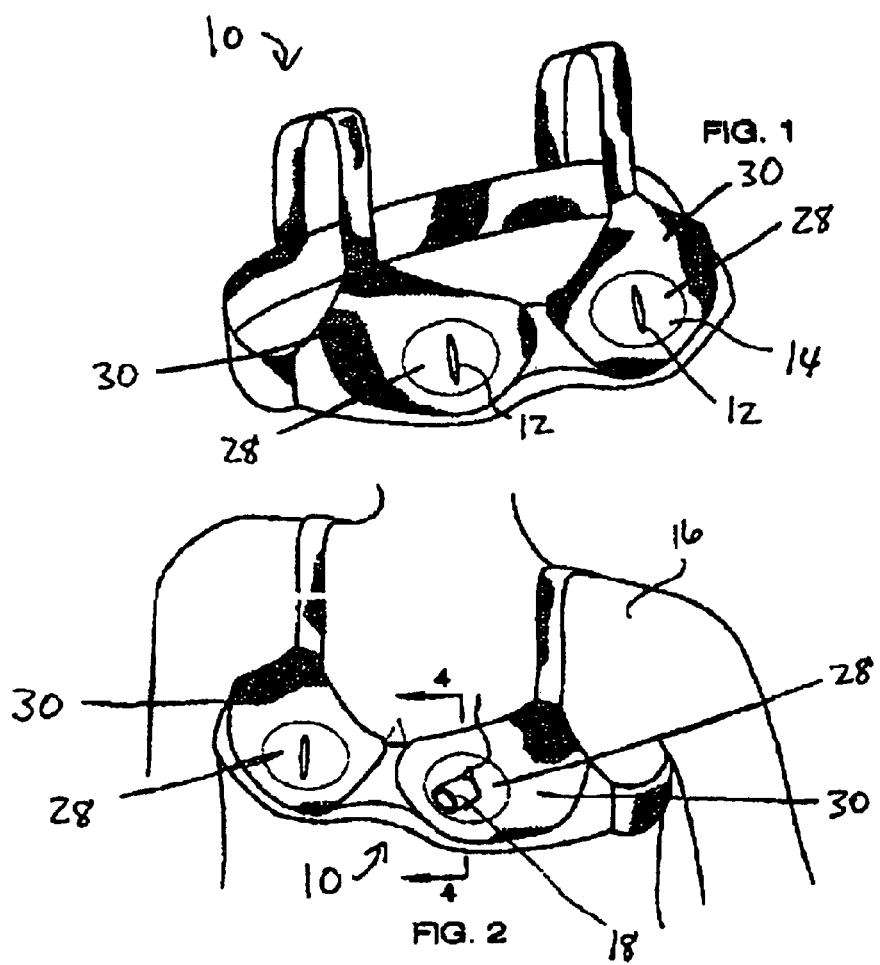

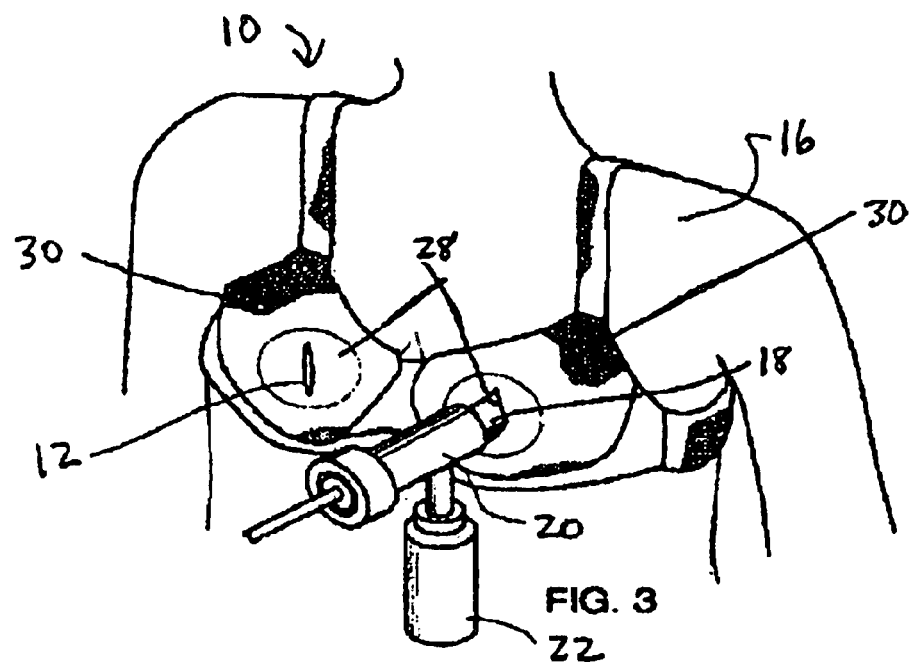
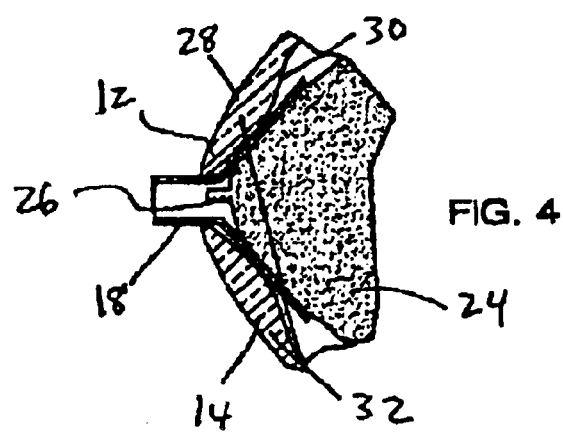

MATERNITY BRA

BACKGROUND OF THE INVENTION

1. Field of the Invention

The present invention relates to a maternity bra for use in connection with pumping breast milk. The maternity bra has particular utility in connection with easily pumping breast milk while the maternity bra is being worn by the mother.

2. Description of the Prior Art

Maternity bras are desirable for meeting the special needs of lactating mothers.

The use of different maternity bras is known in the prior art. For example, U.S. Pat. No. 6,213,840 to Han discloses a hands-free breast pump support bra and system using a highly elastic material. However, the Han '840 patent does not include a padded area structure as advantageously found in the present invention, and has further drawbacks of requiring highly elastic material.

U.S. Pat. No. 5,575,768 to Lockridge et al. discloses a device and kit for supporting a breast shield and related pump equipment that uses a mounting element of elastic bands and loops for providing support. However, the '768 patent does not include a slot and padded area structure, as utilized in the present invention.

Similarly, U.S. Pat. No. 5,514,166 to Silver et al. discloses a different device and method for supporting a breast shield and related pump equipment that implements straps and a bulky flap structure that is very different from the slot and padded area of the present invention.

Furthermore, U.S. Pat. No. 6,247,996 to Fields discloses a breast milk pump support harness that includes detachable milk pump support assemblies that are also very different from the elegant slot and padded area solution of the present invention. Lastly, U.S. Pat. No. 6,004,186 to Penny discloses an apparatus for securing suction devices to a nursing mother's breasts. However, the Penny '186 patent is a halter top, and not a maternity bra. It also has the additional deficiency of using round openings rather than slots.

While the above-described devices fulfill their respective, particular objectives and requirements, the aforementioned patents do not describe a maternity bra that allows breast milk to be pumped conveniently and easily in a hand-free manner by the mother while experiencing the comfort of a padded area as in the present invention.

Therefore, a need exists for a new and improved maternity bra that can be used for hands-free use of a breast pump. In this regard, the present invention substantially fulfills this need. In this respect, the maternity bra according to the present invention substantially departs from the conventional concepts and designs of the prior art, and in doing so provides an apparatus primarily developed for the purpose of improved comfort and convenience of breast pumping for lactating mothers.

SUMMARY OF THE INVENTION

In view of the foregoing disadvantages inherent in the known types of other maternity bras now present in the prior art, the present invention provides an improved maternity bra, and overcomes the above-mentioned disadvantages and drawbacks of the prior art. As such, the general purpose of the present invention, which will be described subsequently in greater detail, is to provide a new and improved maternity bra and method which has all the advantages of the prior art mentioned heretofore and many novel features that result in a maternity bra which is not anticipated, rendered obvious, suggested, or even implied by the prior art, either alone or in any combination thereof.

To attain this, the present invention essentially comprises a kit for a system for pumping breast milk that includes a pump funnel adapted for use in pumping breast milk and a bra. The bra has a slot in the approximate center of each breast section and a padded area surrounding each slot. Each slot is adapted to provide access for the breast pump funnel, and each padded area is adapted to provide extra support for the pump funnel while engaged.

Additionally, the invention encompasses a bra for use while pumping breast milk including a slot in the approximate center of each breast section and a padded area surrounding each slot. Each slot is adapted to provide access for the breast pump funnel, and each padded area is adapted to provide extra support for the pump funnel while engaged.

Finally, also included is a method of pumping breast milk that includes the steps of wearing a bra having a slot in the approximate center of each breast section and a padded area surrounding each slot, such that each slot is adapted to provide access for the breast pump funnel and each padded area is adapted to provide extra support for the pump funnel while engaged; inserting a pump funnel through the slot, wherein the pump funnel is adapted for pumping breast milk; and pumping breast milk through the funnel.

There has thus been outlined, rather broadly, the more important features of the invention in order that the detailed description thereof that follows may be better understood and in order that the present contribution to the art may be better appreciated.

There are, of course, additional features of the invention that will be described hereinafter and which will form the subject matter of the claims attached.

Numerous objects, features and advantages of the present invention will be readily apparent to those of ordinary skill in the art upon a reading of the following detailed description of presently preferred, but nonetheless illustrative, embodiments of the present invention when taken in conjunction with the accompanying drawings. In this respect, before explaining the current embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved maternity bra that has all of the advantages of the prior art other maternity bras and breast pump supports and none of the disadvantages.

It is another object of the present invention to provide a new and improved maternity bra that may be easily and efficiently manufactured and marketed.

An even further object of the present invention is to provide a new and improved maternity bra that has a low cost of manufacture with regard to both materials and labor, and which accordingly is then susceptible of low prices of sale to the consuming public, thereby making such maternity bra economically available to the buying public.

Still another object of the present invention is to provide a new maternity bra that provides in the apparatuses and methods of the prior art some of the advantages thereof, while simultaneously overcoming some of the disadvantages normally associated therewith.

These together with other objects of the invention, along with the various features of novelty that characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a perspective view of the preferred embodiment of the maternity bra constructed in accordance with the principles of the present invention.

FIG. 2 is a perspective view of the maternity bra of the present invention being worn and with a breast pump funnel spout inserted through one of the slots.

FIG. 3 is a perspective view of the maternity bra of the present invention being worn, with a breast pump funnel spout inserted through one of the slots, and with a breast pump and baby bottle connected to the funnel.

FIG. 4 is a cross-section view of the maternity bra of the present invention being worn and with a breast pump funnel spout inserted through the cross-sectioned slot.

The same reference numerals refer to the same parts throughout the various figures.

DESCRIPTION OF THE PREFERRED EMBODIMENT

Referring now to the drawings, and particularly to FIGS. 1–4, a preferred embodiment of the maternity bra of the present invention is shown and generally designated by the reference numeral 10.

In FIG. 1, a new and improved maternity bra 10 of the present invention for comfortable hands-free breast pumping is illustrated and will be described. More particularly, the maternity bra 10 has two slots 12, one in each bra cup or breast covering 30. Each slot 12 is intended to be located in approximate alignment with the wearer's nipple. While this location may vary from implementation to implementation depending upon the shape of the bra cup 30 and the amount of covering each bra cup 30 provides, in the preferred embodiment, each slot 12 is located in the center of its bra cup 30. Surrounding each slot 12 is a padded area 14. The padded area 14 consists of a pad cover 28 affixed to the exterior of each bra cup 30 and padding 32 (not shown) removably enclosed by the pad cover 28 and bra cup 30. The padded areas 14 serve a two-fold function. First, they increase the comfort of the wearer while wearing the maternity bra 10 and simultaneously breast pumping. Second, they provided added support for a breast pump 20 (not shown), thereby improving the hands-free advantage of the present invention.

FIG. 2 shows the maternity bra 10 being worn by a lactating mother 16. A funnel spout 18 has been inserted through the slot 12 so that it is in position with the wearer's nipple 26 (not shown) for pumping.

Turning to FIG. 3, the kit of the present invention is illustrated during use. In use, the funnel 18 is inserted through one of the slots 12 and placed over a nipple 26 (not shown) of the wearer 16. A breast pump 20 is connected to the funnel 18 for pumping milk from the nipple (not shown) of the wearer 16, and a container, such as a baby bottle 22, is connected to the breast pump 20 for receiving the pumped milk from the wearer 16.

FIG. 4 shows a cross section taken along axis 4—4 of FIG. 2, depicting the funnel 18 inserted through slot 12 so as to be mated to a breast 24 in alignment with a nipple 26 of a user 16. A padded area 14 is shown, which consists of a pad cover 28 affixed to the exterior of the bra cup 30 and padding 32 sandwiched between the pad cover 28 and the exterior of the bra cup 30. The padding 32 and bra cup 30 both have slots 12 in them that correspond with the slot 12 in the pad cover 28. The padded area provides additional support for funnel 18, and may also provide cosmetic enhancement, and additional support, comfort and protection for the breasts 24 of a wearer. The padding 32 may be formed of a cotton filler and be permanently affixed into said bra or constitute removable filler that can be inserted and removed through the slot 12 in the pad cover 28.

While a preferred embodiment of the maternity bra has been described in detail, it should be apparent that modifications and variations thereto are possible, all of which fall within the true spirit and scope of the invention. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention. For example, the maternity bra may be composed of cotton. Likewise, the slots could be reinforced. The padded areas may be filled with cotton filler. Alternatively, the padded areas may contain permanent filler. Likewise, the filler may be removable.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed is:

1. A kit for a system for pumping breast milk comprising:
  a pump funnel adapted for use in pumping breast milk;
  a bra comprising:
    a breast-covering section having an exterior with a slot formed therein, wherein said slot is positioned to provide access to a nipple of a wearer, and wherein each slot is adapted to provide access for the breast pump funnel; and
    a padded area surrounding said slot, wherein said padded area comprises a pad cover having a slot formed therein affixed to said exterior of said breast-covering section and padding having a slot formed therein removably secured by said pad cover against said exterior of said breast-covering section, and wherein said padded area is adapted to provide extra support for said pump funnel when said pump funnel is used on a wearer of said bra and said padding can be inserted and removed through said slot in said pad cover.

2. The kit of claim 1, wherein said bra is composed of cotton.

3. The kit of claim 1, wherein said padding is cotton filler.

4. A bra for use while pumping breast milk comprising:
a pair of breast-covering sections, each of said breast-covering sections having an exterior with a slot formed therethrough, wherein said slots are positioned to provide access to nipples of a wearer, and wherein said slots are adapted to provide access for the breast pump funnel; and
a padded area surrounding each of said slots, wherein said padded area comprises a pad cover having a slot formed therein affixed to said exterior of said breast-covering section and padding having a slot formed therein removably secured by said pad cover against said exterior of said breast-covering section, and wherein said padded area is adapted to provide extra support for a pump funnel of a breast pump when the breast pump is used by a wearer of said bra and said padding can be inserted and removed through said slot in said pad cover.

5. The bra of claim 4, wherein said bra is composed of cotton.

6. The bra of claim 4, wherein said padding pad is cotton filler.

7. A method of pumping breast milk comprising the steps of:
wearing a bra having:
a breast-covering section, said breast-covering section having an exterior with a slot formed therethrough, wherein said slot is positioned to provide access to a nipple, and wherein said slot is adapted to provide access for a funnel of a breast pump; and
a padded area surrounding said slot, wherein said padded area comprises a pad cover having a slot formed therein affixed to said exterior of said breast-covering section and padding having a slot formed therein removably secured by said pad cover against said exterior of said breast-covering section, and wherein said padded area is adapted to provide extra support for the pump funnel and said pad can be inserted and removed through said slot in said pad cover;
inserting a funnel adapted for pumping breast milk through said slots; and
pumping breast milk through the funnel.

8. The method of claim 7, wherein the bra is composed of cotton.

9. The method of claim 7, wherein said padding is cotton filler.

* * * * *